United States Patent
Green et al.

(10) Patent No.: US 7,498,329 B2
(45) Date of Patent: Mar. 3, 2009

(54) SALT FORM OF DOPAMINE AGONIST

(75) Inventors: Stuart Peter Green, Sandwich (GB);
Olivier Alain Lazzari, Sandwich (GB);
Duncan Charles Miller, Sandwich (GB); Fabrice Henri Salingue, Sandwich (GB)

(73) Assignee: Pfizer Inc., New York, NY (US)

( * ) Notice: Subject to any disclaimer, the term of this patent is extended or adjusted under 35 U.S.C. 154(b) by 427 days.

(21) Appl. No.: 11/349,324

(22) Filed: Feb. 6, 2006

(65) Prior Publication Data

US 2006/0183740 A1      Aug. 17, 2006

Related U.S. Application Data

(60) Provisional application No. 60/654,200, filed on Feb. 18, 2005.

(30) Foreign Application Priority Data

Feb. 7, 2005     (GB)  .................. 0502509.3

(51) Int. Cl.
*A61K 31/5377*   (2006.01)
*C07D 413/04*    (2006.01)

(52) U.S. Cl. ............ 514/235.5; 544/106; 544/111; 544/124; 514/231.2; 514/231.5

(58) Field of Classification Search ......... 544/106, 544/111, 124; 514/231.2, 231.5, 235.5
See application file for complete search history.

(56) References Cited

U.S. PATENT DOCUMENTS 7,323,462 B2 * 1/2008 Allerton et al. .......... 514/235.2

FOREIGN PATENT DOCUMENTS

| WO | WO 2004 052372 | 6/2004 |
|---|---|---|
| WO | WO 2005115985 | 12/2005 |

OTHER PUBLICATIONS

Bennet, et al., *Pain*, "A peripheral mononeuropathy in rat that produces disorders of pain sensation like those seen in man", vol. 33, pp. 87-107, (1988).

Chen, et al., *Journal of Neurophysiology*, "Hypersensitivity of Spinothalamic Tract Neurons Associated With Diabetic Neuropathic Pain in Rats", vol. 87(6): pp. 2726-2733, (2002).

Field, et al., *Pain*, "Detection of static and dynamic components of mechanical allodynia in rat models of neuropathic pain: are they signalled by distinct primary sensory neurones?", vol. 83(2), pp. 303-311 (1999).

Houge, et al., *Annals of Pharmacotherapy*, "Pathophysiology and First Line Treatment of Osteoarthritis", vol. 36, pp. 679-686, (2002).

Meyer, et al., *Textbook of Pain*, "Peripheral neural mechanisms of nociception", pp. 13-44 (1994).

Millan, Mark., *Progress in Neurobiology*, "The Induction of Pain: An Integrative Review", vol. 57, pp. 1-164, (1999).

Woolf, et al., *Pain Supplement*, vol. 6, pp. S141-S147, (1999).

Woolf, et al., *Science*, "Neuronal Plasticity: Increasing the Gain in Pain".vol. 288, pp. 1765-1768, (2000).

Woolf, et al., *Lancet*, "Neuropathic pain: aetiology, symptoms, mechanisms, and management", vol. 353, pp. 1959-1964, (1999).

* cited by examiner

*Primary Examiner*—Golam M Shameem
(74) *Attorney, Agent, or Firm*—Gregg C. Benson; A. Dean Olson

(57) ABSTRACT

This invention relates to a novel salt form of dopamine agonist 5-[(2R,5S)-5-methyl-4-propylmorpholin-2-yl]pyridin-2-amine (I):

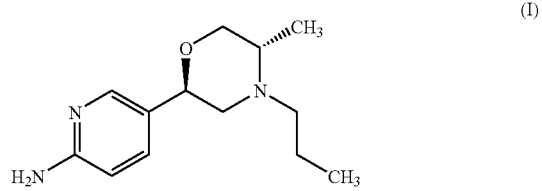

More particularly, this invention relates to 5-[(2R,5S)-5-methyl-4-propylmorpholin-2-yl]pyridin-2-amine di-(1S)-camphorsulfonate (di-S-camsylate) and to processes for the preparation of, intermediates used in the preparation of, compositions containing, and the uses of this salt.

6 Claims, 6 Drawing Sheets

Isothermal Gravimetric analysis of 5-[(2R,5S)-5-methyl-4-propylmorpholin-2-yl]pyridin-2-amine Di-S-Camsylate Monohydrate at 40, 45, 80 and 85°C

Water Sorption of 5-[(2R,5S)-5-methyl-4-propylmorpholin-2-yl]pyridin-2-amine Di-S-Camsylate Monohydrate) at 30°C

Comparison of the Water Sorption of 5-[(2R,5S)-5-methyl-4-propylmorpholin-2-yl]pyridin-2-amine Di-S-Camsylate Monohydrate with the Free Base, di-D-Tartrate, and Hydrobromide Salt at 30°C

Simulated PXRD Pattern for 5-[(2R,5S)-5-methyl-4-propylmorpholin-2-yl]pyridine-2-amine di-S-camsylate monohydrate

Actual PXRD Pattern for 5-[(2R,5S)-5-methyl-4-propylmorpholin-2-yl]pyridin-2-amine di-S-camsylate monohydrate

DSC Thermogram for 5-[(2R,5S)-5-methyl-4-propylmorpholin-2-yl]pyridin-2-amine Di-S-Camsylate Monohydrate

SALT FORM OF DOPAMINE AGONIST

This application claims priority from United Kingdom Provisional Application Number GB0502509.3, filed Feb. 7, 2005, and U.S. Provisional Application No. 60/654,200 filed Feb. 18, 2005.

The entire disclosure of the above parent applications are fully incorporated herein by reference thereto.

This invention relates to a novel salt form of dopamine agonist 5-[(2R,5S)-5-methyl-4-propylmorpholin-2-yl]pyridin-2-amine (I):

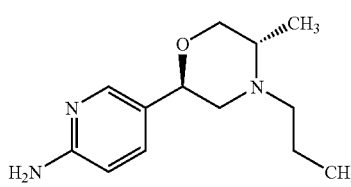

More particularly, this invention relates to 5-[(2R,5S)-5-methyl-4-propylmorpholin-2-yl]pyridin-2-amine di-(1S)-camphorsulfonate (di-S-camsylate) and to processes for the preparation of, intermediates used in the preparation of, compositions containing, and the uses of this salt.

According to the specification of International Patent Application WO2004/052372 it has been shown that the compound of formula (I) is a selective D3 agonist, useful for the treatment and/or prevention of sexual dysfunction, for example female sexual dysfunction (FSD), in particular female sexual arousal disorder (FSAD) and male sexual dysfunction, in particular male erectile dysfunction (MED). Male sexual dysfunction as referred to herein is meant to include ejaculatory disorders such as premature ejaculation, anorgasmia (inability to achieve orgasm) or desire disorders such as hypoactive sexual desire disorder (HSDD; lack of interest in sex). Female sexual dysfunction as referred to herein is meant to include hypoactive sexual desire disorder, sexual arousal disorder, orgasmic disorders and sexual pain disorders. This compound is also useful in treating neuropsychiatric disorders and neurodegenerative disorders.

The free-base form of the compound 5-[(2R,5S)-5-methyl-4-propylmorpholin-2-yl]pyridin-2-amine has a low melting point and is also deliquescent. These properties make the compound an undesirable choice for inclusion in a pharmaceutical formulation.

Remarkably, it has been found that 5-[(2R,5S)-5-methyl-4-propylmorpholin-2-yl]pyridin-2-amine di-S-camsylate monohydrate has the advantage of possessing the required properties to enable it to be formulated as a pharmaceutical. Namely, it is not deliquescent, it has a high melting point, it is non-hygroscopic, and it is crystalline in form.

Moreover, 5-[(2R,5S)-5-methyl-4-propylmorpholin-2-yl]pyridin-2-amine di-S-camsylate monohydrate possesses the following additional advantageous properties that make it even more amenable to the conditions employed in the commercial scale manufacture of a pharmaceutical drug product, namely:

It does not dehydrate after 3.5 hours under conditions of 0% relative humidity (RH) at 30° C. Typically a pharmaceutical hydrate would be expected to dehydrate within a few hours of exposure to 0% RH. Furthermore, upon heating a sample of 5-[(2R,5S)-5-methyl-4-propylmorpholin-2-yl]pyridin-2-amine di-S-camsylate monohydrate in a flow of 0% RH, the dehydration event was observed at 85° C. This is a much higher temperature than would normally be expected for a hydrated salt. Such kinetic stability is desirable for allowing the compound to be successfully milled prior to formulation.

Many hydrates are not stable to the harsh vacuum drying conditions required in the isolation of a pharmaceutical drug product. However, 5-[(2R,5S)-5-methyl-4-propylmorpholin-2-yl]pyridin-2-amine di-S-camsylate monohydrate would be stable in such a process as, upon exposure to reduced partial pressure at 40° C., the hydrate remains down to 10 mbar.

The present invention comprises the following embodiments:

a) 5-[(2R,5S)-5-methyl-4-propylmorpholin-2-yl]pyridin-2-amine di-S-camsylate:

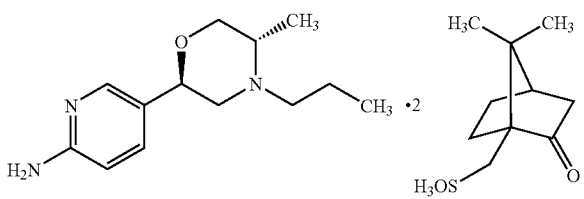

b) The compound according to a) in the form of a monohydrate.

c) The compound according to b) having characteristic main peaks in its powder X-ray diffraction pattern of 6.3, 12.7, 15.1, 16.3 and 25.6 degrees 2θ.

d) The compound according to a), b) or c) having an enantiomeric excess of at least 80%.

e) The compound according to d) having an enantiomeric excess of at least 95%.

f) A pharmaceutical composition comprising 5-[(2R,5S)-5-methyl-4-propylmorpholin-2-yl]pyridin-2-amine di-S-camsylate and a pharmaceutically acceptable diluent or carrier.

g) A pharmaceutical composition according to f), wherein 5-[(2R,5S)-5-methyl-4-propylmorpholin-2-yl]pyridin-2-amine di-S-camsylate is in the form of a monohydrate.

h) A process for the preparation of 5-[(2R,5S)-5-methyl-4-propylmorpholin-2-yl]pyridin-2-amine di-S-camsylate monohydrate, comprising the reaction of a compound of formula (X)

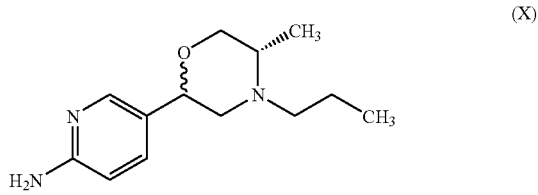

with (1S)-10-camphorsulfonic acid in a suitable solvent.

i) A process according to h) wherein the solvent is acetone/water.

j) A process according to i) wherein the amount of water used is in the range of 0.7 L to 1 L water per Kg of 5-[(2R,5S)-5-methyl-4-propylmorpholin-2-yl]pyridin-2-amine.

k) A process according to i) wherein the amount of water used is in the range of 0.8 L to 0.9 L water per Kg of 5-[(2R,5S)-5-methyl-4-propylmorpholin-2-yl]pyridin-2-amine.

l) A compound of formula (VII)

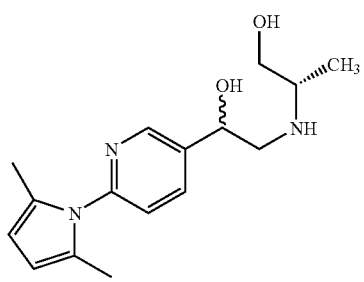

and pharmaceutically acceptable salts and solvates thereof.

The compound of the invention can exist, depending on the atmospheric conditions (temperature and humidity), in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Accordingly, the present invention additionally comprises the pharmaceutically acceptable solvates of 5-[(2R,5S)-5-methyl-4-propylmorpholin-2-yl]pyridin-2-amine di-S-camsylate and 5-[(2R,5S)-5-methyl-4-propylmorpholin-2-yl]pyridin-2-amine di-S-camsylate monohydrate.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The invention also includes all polymorphs and crystal habits of 5-[(2R,5S)-5-methyl-4-propylmorpholin-2-yl]pyridin-2-amine di-S-camsylate and 5-[(2R,5S)-5-methyl-4-propylmorpholin-2-yl]pyridin-2-amine di-S-camsylate monohydrate.

The present invention includes all pharmaceutically acceptable isotopically-labelled compounds of 5-[(2R,5S)-5-methyl-4-propylmorpholin-2-yl]pyridin-2-amine di-S-camsylate and its monohydrate, wherein one or more atoms are replaced by atoms having the same atomic number, but an atomic mass or mass number different from the atomic mass or mass number which predominates in nature.

Examples of isotopes suitable for inclusion in the compound of the invention include isotopes of hydrogen, such as $^2$H and $^3$H, carbon, such as $^{11}$C, $^{13}$C and $^{14}$C, nitrogen, such as $^{13}$N and $^{15}$N, oxygen, such as $^{15}$O, $^{17}$O and $^{18}$O, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of 5-[(2R,5S)-5-methyl-4-propylmorpholin-2-yl]pyridin-2-amine di-S-camsylate can generally be prepared by conventional techniques known to those skilled in the art or by processes analogous to those described in the accompanying experimental using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

5-[(2R,5S)-5-methyl-4-propylmorpholin-2-yl]pyridin-2-amine di-S-camsylate monohydrate may be prepared according to the following scheme. Those skilled in the art may be aware of other synthetic methods that may be equally as practicable.

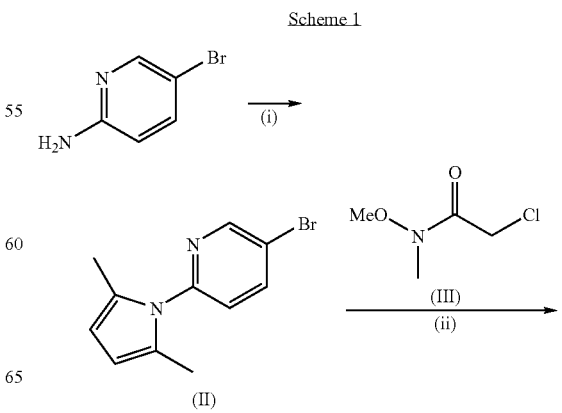

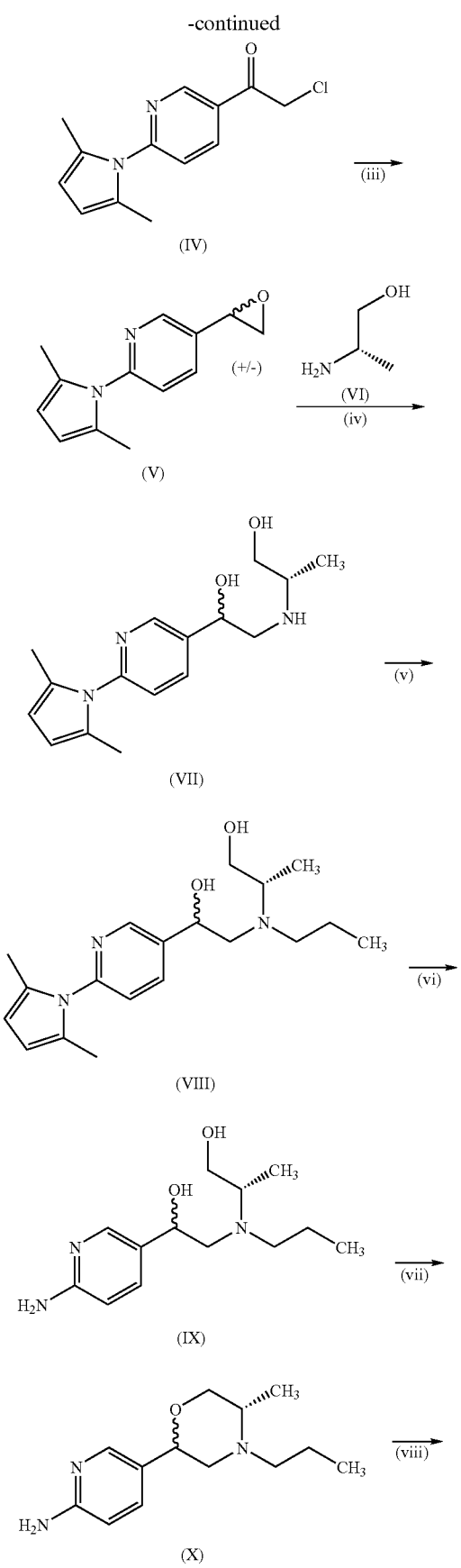

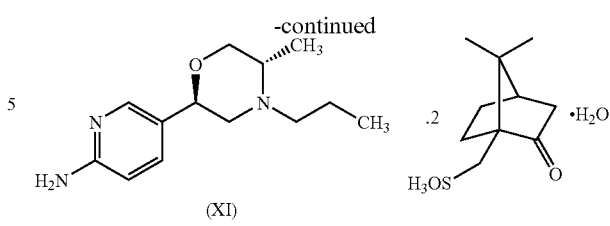

2-Amino-5-bromopyridine is allowed to react with (i) 2,5-hexanedione and p-oluenesulfonic acid, under Dean-Stark conditions in a suitable solvent (such as heptane), to give protected bromo-pyridine (II). Bromo-pyridine (II) is then treated with (ii) n-butyl lithium in a suitable solvent (such as tertiary-butyl methyl ether) at reduced temperature. A solution of amide (III) is then added, to yield chloro ketone (IV). This ketone is then converted to epoxide (V) by (iii) reduction with a suitable reducing agent (such as sodium borohydride), in a suitable solvent (such as tetrahydrofuran); followed by treatment with a suitable base (such as sodium hydroxide). Epoxide (V) is subjected to (iv) nucleophilic attack with (S)-(+)-2-amino-1-propanol (VI) in a suitable solvent (such as tetrahydrofuran) at elevated temperature to give amine (VII). Amine (VII) is then converted to compound (VIII) by (v) reductive alkylation with propionaldehyde in the presence of a suitable reducing agent (such as sodium triacetoxyborohydride). Compound (VIII) is converted to compound (IX) by (vi) deprotection with hydroxylamine in a suitable solvent (such as ethanol), at elevated temperature. Compound (X) is generated by (vii) cyclisation of compound (IX) under acidic conditions. Finally, 5-[(2R,5S)-5-methyl-4-propylmorpholin-2-yl]pyridin-2-amine di-S-camsylate monohydrate (XI), is generated by (viii) reaction of compound (X) with (1S)-10-camphorsulfonic acid in a suitable solvent (such as acetone/water), followed by crystallization of the salt.

5-[(2R,5S)-5-methyl-4-propylmorpholin-2-yl]pyridin-2-amine di-S-camsylate and polymorphs and pharmaceutically acceptable solvates thereof have utility as a selective D3 agonist in the treatment of disease states.

Accordingly, in a first additional embodiment, the present invention provides for the use of 5-[(2R,5S)-5-methyl-4-propylmorpholin-2-yl]pyridin-2-amine di-S-camsylate and polymorphs and pharmaceutically acceptable solvates thereof, in medicine.

5-[(2R,5S)-5-methyl-4-propylmorpholin-2-yl]pyridin-2-amine di-S-camsylate and polymorphs, and pharmaceutically acceptable solvates thereof, may be particularly suitable for treating female sexual dysfunction, male erectile dysfunction, pain, neurodegeneration, depression and psychiatric disorders.

Accordingly, in a second additional embodiment, the present invention provides for the use of 5-[(2R,5S)-5-methyl-4-propylmorpholin-2-yl]pyridin-2-amine di-S-camsylate and polymorphs, and pharmaceutically acceptable solvates thereof, in the manufacture of a medicament for the treatment and/or prevention of sexual dysfunction; suitable conditions including, female sexual dysfunction (FSD), in particular female sexual arousal disorder (FSAD) and male sexual dysfunction, in particular male erectile dysfunction (MED). Male sexual dysfunction as referred to herein is meant to include ejaculatory disorders such as premature ejaculation, anorgasmia (inability to achieve orgasm) or desire disorders such as hypoactive sexual desire disorder (HSDD; lack of interest in sex). Female sexual dysfunction as referred to herein is meant to include hypoactive sexual desire disorder, sexual arousal disorder, orgasmic disorders and sexual pain disorders.

In a third additional embodiment, the present invention provides for the use of 5-[(2R,5S)-5-methyl-4-propylmorpholin-2-yl]pyridin-2-amine di-S-camsylate and polymorphs and pharmaceutically acceptable solvates thereof, in the preparation of a medicament for treating male erectile dysfunction.

In a fourth additional embodiment, the present invention provides for the use of 5-[(2R,5S)-5-methyl-4-propylmorpholin-2-yl]pyridin-2-amine di-S-camsylate and polymorphs and pharmaceutically acceptable solvates thereof, in the preparation of a medicament for treating female sexual dysfunction, in particular female sexual arousal disorder and hypoactive sexual desire disorder.

The salt of the present invention may also have utility in the treatment of pain, particularly, but not limited to, chronic nociceptive pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other Types of Pain Include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

Accordingly, in a fifth additional preferred embodiment, the present invention may also provide for the use of 5-[(2R, 5S)-5-methyl-4-propylmorpholin-2-yl]pyridin-2-amine di-S-camsylate and polymorphs and pharmaceutically acceptable solvates thereof, in the preparation of a medicament for the treatment or prevention of pain. Furthermore the present invention may also provide for the use of 5-[(2R,5S)-5-methyl-4-propylmorpholin-2-yl]pyridin-2-amine di-S-camsylate and polymorphs and pharmaceutically acceptable solvates thereof, in the preparation of a medicament for the treatment or prevention of chronic nociceptive pain.

In a sixth additional preferred embodiment, the present invention may also provide for the use of 5-[(2R,5S)-5-methyl-4-propylmorpholin-2-yl]pyridin-2-amine di-S-camsylate and polymorphs and pharmaceutically acceptable solvates thereof, in the preparation of a medicament for treating neuropsychiatric disorders or neurodegenerative disorders; suitable conditions may include hypertension, neurodegeneration, psychiatric disorders, depression (e.g. depression in cancer patients, depression in Parkinson's patients, postmyocardial infarction depression, subsyndromal symptomatic depression, depression in infertile women, major depression, child abuse induced depression, post partum depression and grumpy old man syndrome), single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; trichotillomania, kleptomania, attention deficit hyperactivity disorder (ADHD); behavioral disturbances associated with mental retardation, autistic disorder; borderline personality disorder; avoidant personality disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; emotional lability, pathological crying; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; eating disorders (e.g. anorexia nervosa and bulimia nervosa), obesity; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy; Restless Leg Syndrome, Huntington's disease, Multiple Sclerosis, mild cognitive impairment, Down's syndrome, stroke, Hereditary Cerebral Hemorrhage with Amyloidosis of the Dutch-Type, cerebral amyloid angiopathy, delirium, dementia, age-related cognitive decline (ARCD), and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, dementias of mixed vascular and degenerative origin, dementia associated with Parkinson's disease, dementia associated with progressive supranuclear palsy, dementia associated with cortical basal degeneration, multi-infarct dementia, alcoholic dementia or other drug-related dementia, dementia associated with intracranial tumors or cerebral trauma, dementia associated with Huntington's disease, Pick's disease, Creutzfeldt-Jakob disease, HIV or AIDS-related dementia, diffuse Lewy body type of Alzheimer's disease, frontotemporal dementias with parkinsonism (FTDP), head trauma, spinal cord injury, demyelinating diseases of the nervous system, peripheral neuropathy, pain, cerebral amyloid angiopathy, amyotrophic lateral sclerosis, multiple sclerosis, dyskinesia associated with dopamine agonist therapy, mental retardation, learning disorders, including reading disorder, mathematics disorder, or a disorder of written expression; age-related cognitive decline, amnesic disorders, neuroleptic-induced parkinsonism, tardive dyskinesias, and acute and chronic neurodegenerative disorders; premenstrual syndrome, fibromyalgia syndrome, stress incontinence, endocrine disorders (e.g. hyperprolactinaemia), vasospasm (particularly in the cerebral vasculature), cerebellar ataxia, gastrointestinal tract disorders (involving changes in motility and secretion), cluster headache, migraine, pain, chronic paroxysmal hemicrania, headache (associated with vascular disorders), sleeping disorder (cataplexy) and shock.

In a further embodiment, the present invention additionally includes the uses recited above wherein 5-[(2R,5S)-5-methyl-4-propylmorpholin-2-yl]pyridin-2-amine di-S-camsylate is in the form of a monohydrate.

Activity at the dopamine D3 receptor may be determined using the methods described in WO 2004/052372, which is incorporated herein by reference. Using this assay, 5-[(2R,5S)-5-methyl-4-propylmorpholin-2-yl]pyridin-2-amine di-S-camsylate monohydrate has a functional potency at D3 receptor expressed as an EC50, of 21 nM and 476 fold selectivity for D3 over D2. Selectivity is calculated as the D2 EC50 value divided by the D3 EC50 value.

Suitable assays for determining the utility of the compounds of the invention in various pain conditions are described below:

Neuropathic Pain

The activity of a compound in the treatment of neuropathic pain may be measured according to the following test protocol.

Animals: Male Sprague Dawley rats are housed in groups. All animals are kept under a 12 h light/dark cycle (lights on at 07 h 00 min) with food and water ad libitum. All experiments were carried out by an observer blind to the treatments and in accordance with the Home Office Animals (Scientific Procedures) Act 1986.

Chronic Constriction Injury (CCI) Rat Model of Neuropathic Pain

The CCI of sciatic nerve was performed as previously described by Bennett and Xie (Bennett G J, Xie Y K. A peripheral mononeuropathy in rat that produces disorders of pain sensation like those seen in man. Pain:33:87-107, 1988). Animals were anaesthetised with a 2% isofluorane/O2 mixture. The right hind thigh was shaved and swabbed with 1% iodine. Animals were then transferred to a homeothermic blanket for the duration of the procedure and anaesthesia maintained during surgery via a nose cone. The skin was cut along the line of the thighbone. The common sciatic nerve was exposed at the middle of the thigh by blunt dissection through biceps femoris. About 7 mm of nerve was freed proximal to the sciatic trifurcation, by inserting forceps under the nerve and the nerve gently lifted out of the thigh. Suture was pulled under the nerve using forceps and tied in a simple knot until slight resistance was felt and then double knotted. The procedure was repeated until 4 ligatures (4-0 silk) were tied loosely around the nerve with approx 1 mm spacing. The incision was closed in layers and the wound treated with topical antibiotics.

Streptozocin (STZ)-induced Diabetes Neuropathy in the Rat

Diabetes was induced by a single intraperitoneal injection of streptozotocin (50 mg/kg) freshly dissolved in 0.9% sterile saline. Streptozotocin injection induces a reproducible mechanical allodynia within 3 weeks, lasting for at least 7 weeks (Chen S R and Pan H L. Hypersensitivity of Spinothalamic Tract Neurons Associated With Diabetic Neuropathic Pain in Rats. J Neurophysiol 87: 2726-2733, 2002).

Assessment of Static and Dynamic Allodynia

Static Allodynia

Animals were habituated to wire bottom test cages prior to the assessment of allodynia. Static allodynia was evaluated by application of von Frey hairs (Stoelting, Wood Dale, Ill., USA.) in ascending order of force (0.6, 1, 1.4, 2, 4, 6, 8, 10, 15 and 26 grams) to the plantar surface of hind paws. Each von Frey hair was applied to the paw for a maximum of 6 sec, or until a withdrawal response occurred. Once a withdrawal response to a von Frey hair was established, the paw was re-tested, starting with the filament below the one that produced a withdrawal, and subsequently with the remaining filaments in descending force sequence until no withdrawal occurred. The highest force of 26 g lifted the paw as well as eliciting a response, thus represented the cut off point. Each animal had both hind paws tested in this manner. The lowest amount of force required to elicit a response was recorded as paw withdrawal threshold (PWT) in grams. Static allodynia was defined as present if animals responded to a stimulus of, or less than, 4 g, which is innocuous in naive rats (Field M J, Bramwell S, Hughes J, Singh L. Detection of static and dynamic components of mechanical allodynia in rat models of neuropathic pain: are they signalled by distinct primary sensory neurones? Pain, 1999;83:303-11).

Dynamic Allodynia

Dynamic allodynia was assessed by lightly stroking the plantar surface of the hind paw with a cotton bud. To avoid recording general motor activity, care was taken to perform this procedure in fully habituated rats that were not active. At least two measurements were taken at each time point, the mean of which represented the paw withdrawal latency (PWL). If no reaction was exhibited within 15 sec the procedure was terminated and animals were assigned this withdrawal time. A pain withdrawal response was often accompanied with repeated flinching or licking of the paw. Dynamic allodynia was considered to be present if animals responded to the cotton stimulus within 8 sec of commencing stroking (Field et al, 1999).

Nociceptive Pain

The activity of a compound in the treatment of nociceptive pain may be measured according to the following test protocols.

Hotplate

Experimental Procedure: Male Sprague Dawley rats are placed on a hot plate (Ugo Basile, Italy) maintained at 55±5° C. The time between placement of the animal on the hot plate and occurrence of either licking of fore or hind paw, shaking or jumping off the surface is measured. Baseline measurements will be made and animals reassessed following drug administration. The cut off time for hot plate latencies is set at 20 seconds to prevent tissue damage.

Ovariohysterectomy (OVX)

Experimental Procedure: Female Sprague Dawley rats are placed into an anaesthetic chamber and anaesthetised with a 2% isofluorane/$O_2$ mixture. During surgery, anaesthesia is maintained via a nose cone. OVX is performed via a midline incision (2 cm in length) in the linea alba, whilst the animal is on a heat blanket. The ovarian ligaments and cervix are ligated with 5-0 silk, using a single clamp technique. The ovaries and uterus are then removed. The abdominal wall is closed using 4 simple interrupted sutures and the skin closed using 4 wound clips. Immediately after surgery animals are placed in individual plexiglass chambers. Once the animal has recovered from the anaesthetic the abdominal body postures are recorded in 30 min bins at various time points. Postures scored are humpback position, contraction of the muscle of the abdomen associated with inward movements of the hind limb, stretching of the body and squashing of the lower abdomen against the floor. Each of these behaviours is scored as one posture.

Brennan

Experimental Procedure: Male Sprague Dawley rats are placed into an anaesthetic chamber and anaesthetised with a 2% isofluorane/$O_2$ mixture. During surgery, anaesthesia is maintained via a nose cone. The plantar aspect of the right hind paw is cleaned with 50% ethanol. A 1 cm long longitudinal incision is made with a number 11 blade through the skin and fascia of the plantar aspect of the foot, starting 0.5 cm from the proximal edge of the heel and extending toward the toes. The plantaris muscle is elevated using forceps and incised longitudinally, the muscle origin and insertion remain intact. After haemostasis with gentle pressure, the skin is closed with two simple sutures of braided silk.

Mono-iodoacetate (MIA)-induced OA Model

Male 6 weeks-old Sprague-Dawley (SD, Japan SLC or Charles River Japan) rats are anesthetized with pentobarbital. Injection site is shaved and cleaned with 70% ethanol. 25 µl of MIA solution or saline is injected in the right knee joint using a 29 G needle. 7, 14, 19 and 20 days after the MIA injection, train rats to measure the weight bearing (WB) without their stress. 21 days after the MIA injection, the WB on two of each hind paw is measured and the WB deficit is calculated as in 10.2. Define the WB deficit value as "pre value". Arrange for experimental group evenly in consideration of pre value and prepre value. After the administration of test compounds or vehicle, the WB on two of each hind paw was measured.

Cancer Pain Model

These experiments used adult male C3H/HeN mice (Nihon SLC, Shizuoka, Japan). The mice were housed in accordance with National Institutes of Health guidelines in a vivarium maintained at 22° C. with a 12-hour alternating light-dark cycle, and were given food and water ad libitum. The sarcoma injection protocol used has been described. After induction of general anesthesia with an inhalation of isofluran (2%), a superficial incision was made in the skin overlying the patella, using Mora scissors. The patellar ligament was then cut, exposing the condyles of the distal femur. A 30-gauge needle was inserted at the level of the intercondylar notch and into the medullary canal to create an initial core pathway. After the initial core was made, a 29-gauge needle was used to make the final pathway into the bone. A 0.5-mm depression was then made using a half-round bur in a pneumatic dental high speed handpiece, to serve as mechanical retention for the dental resin plug. Then, 20 µl α-minimum essential media (Sigma; sham injection) or 20 µl media containing $1 \times 10^5$ 2472 osteolytic sarcoma cells (American Type Culture Collection, Rockville, Md.; sarcoma injection) was injected using a 29-gauge needle and a 0.25 cc syringe. To prevent leakage of cells outside the bone, the injection site was closed with dental resin, followed by copious irrigation with filtered water. Wound closure was achieved using auto wound clips (Becton Dickinson, San Jose, Calif.). Wound clips were removed at day 5 to prevent interference with behavioral testing.

Assessment of Static and Dynamic Allodynia

Static Allodynia

Procedure as described above for neuropathic pain.

Dynamic Allodynia

Procedure as described above for neuropathic pain.

Radiant Heat Paw Withdrawal

Experimental procedure: Thermal paw withdrawal is assessed using the rat plantar test (Ugo Basile, Italy) following a modified method of Hargreaves et al., 1988. Rats are habituated to the apparatus that consists of three individual perspex boxes on an elevated glass table. A mobile radiant heat source is located under the table and focused onto the hind paw and paw withdrawal latencies (PWL) are recorded. There is an automatic cut off point of 22.5 s to prevent tissue damage. PWL are taken 2-3 times for both hind paws of each animal, the mean of which represents baselines for right and left hind paws. The apparatus is calibrated to give a PWL of approximately 10 s.

Weight Bearing

Experimental procedure: Animals are examined for hypersensitivity in the weight-bearing test, using an "incapacitance tester" (Linton Instruments, Diss, Norfolk, U.K.). Rats were positioned with their fore limbs up on a perspex slope and hind limb weight distribution was measured via force transducers under each of the hind paws. Each animal is placed in the apparatus and the weight load exerted by the hind paws is noted. The difference in weight bearing is calculated by subtracting the ipsilateral (injured) paw from the contralateral paw (normal) and this constitutes the raw data.

Inflammatory Pain

The activity of compound in the treatment of inflammatory pain may be measured according to the following test protocol.

CFA-induced Weight Bearing Deficits in Rats

Male 7-week-old SD rats are fasted overnight. CFA (300 µg of *Mycobacterium Tuberculosis* H37 RA (Difco Laboratories) in 100 µL of liquid paraffin (Wako)) is injected into the rat's right hind footpad. Two days after the administration of CFA, the changes in hind paw weight distribution between the left (ipsilateral) and the right (contralateral) limbs are measured as an index of pain by using Linton Incapacitance tester (Linton Instrumentation, UK). The test compound suspended in 0.1% MC (Wako) is administered orally in a volume of 1 mL per 100 g body weight. Each animal is placed in the apparatus and the weight load exerted by the hind paws is measured before, 1, 2 and 4 hours after drug administration.

Carrageenin-induced Mechanical Hyperalgesia in Rats

Male 4-week-old SD rats are fasted overnight. Hyperalgesia is induced by intraplantar injection of Lambda-carrageenin (0.1 ml of 1% w/v solution in saline, Zushikagaku). The test compound (1 ml of 0.1% methylcellulose/100 g body weight) is given orally at 5.5 hours after the carrageenin injection. The paw withdrawal threshold (gram) is measured by analgesimeter (Ugo Basile) at 3.5, 4.5, 6.5 and 7.5 hours after the carrageenin injection. (Randall L. O. & Selitto I. J., Arch. Int. Pharmacodyn. 111, 409-419, 1957)

Carrageenan-induced Thermal Hyperalgesia (CITH) in the Rat

Thermal hyperalgesia was assessed using the rat plantar test (Ugo Basile, Comerio, Italy), according to a method modified by Hargreaves et al. (1988). Briefly, rats were habituated to the apparatus that consisted of three individual Perspex boxes on a glass table. A mobile radiant heat source was located under the table and focused onto the desired paw. Paw withdrawal latencies (PWLs) were recorded three times for both hind paws of each animal, the mean of which represented baseline for left and right hind paws. The apparatus was calibrated to give a PWL of approximately 10 s in naïve rats. To prevent tissue damage of the plantar zone, a 22.5 sec cut-off was observed. Lambda carrageenan was injected intraplantarly (100 μl, 20 mg/ml) the right hind paw and baseline recordings of PWT were taken 2 hr post administration.

Visceral Pain

The activity of a compound in the treatment of visceral pain may be measured according to the following test protocols.

Several models are available to determine if a compound is effective in treating disorders of the viscera. These models include a LPS model (Eutamene H et al, J Pharmacol Exp Ther 2000 295 (1):162-7), a TNBS model (Diop L. et al, Gastroenterology 1999, 116, 4(2): A986), a IBD model (Clemett D, Markham A, Drugs 2000 April;59(4):929-56), a pancreatic pain model (Isla A M, Hosp Med 2000 June;61(6): 386-9) and a visceral non digestive pain model (Boucher M et al, J Urol 2000 July;164(1):203-8).

TNBS-induced Chronic Visceral Allodynia in Rats

In this experimental model of colonic distension in awake rats, previous injection of trinitrobenzenesulfonic acid (TNBS) into the proximal colon lowered the visceral pain threshold.

Materials and methods: Male Sprague-Dawley rats are used. The animals are housed 3 per cage in a regulated environment (20±1° C., 50±5% humidity, with light 8:00 am to 8:00 pm). At day 0, under anesthesia (ketamine 80 mg/kg i.p.; acepromazine 12 mg/kg i.p.), the injection of TNBS (50 mg/kg in ethanol 30%), or saline (1.5 ml/kg) for control rats, is performed into the proximal colon wall (1 cm from the cecum). After the surgery, animals are individually housed in polypropylene cages and kept in a regulated environment (20±1° C., 50±5% humidity, with light 8:00 a.m. to 8:00 p.m.) during 7 days. At day 7 after TNBS administration, a balloon (5-6 cm length) is inserted by anus, and kept in position (tip of balloon 5 cm from the anus) by taping the catheter to the base of the tail. Oral administration of the test compound is performed 1 h before the colonic distension cycle: the balloon is progressively inflated by steps of 5 mm Hg (0.667 kPa), from 0 to 75 mm Hg, each step of inflation lasting 30 s. Each cycle of colonic distension is controlled by a standard barostat. The threshold (mm Hg) corresponds to the pressure which produced the first abdominal contraction, and the cycle of distension is then discontinued. The colonic threshold is determined after performance of four cycles of distension on the same animal.

LPS-induced Rectal Hypersensitivity in Rats

Intraperitoneal injection of bacterial lipo-polysaccharide (LPS) has been shown to induce rectal hyperalgesia in awake rats.

Materials and methods: Animals are surgically prepared for electromyography: rats are anaesthetized by intraperitoneal injection of acepromazine (0.6 mg/kg) and ketamine (120 mg/kg). Three groups of three electrodes are implanted in the abdominal external oblique musculature, just superior to the inguinal ligament. Electrodes are exteriorized on the back of the neck and protected by a glass tube attached to the skin. Animals are individually housed in polypropylene cages and kept in a temperature-controlled room (21° C.). Food (UAR pellets, Epinay, France) and water are provided ad libitum.

Electromyographic recordings begin five days after surgery. The electrical activity of abdominal striated muscles is recorded with an electroencephalograph machine (Mini VIII Alvar, Paris, France) using a short time constant (0.03 s) to remove low-frequency signals (<3 Hz) and a paper speed of 3.6 cm/min. Spike bursts are recorded as an index of abdominal contractions.

Distension procedure: Rats are placed in plastic tunnels (6 cm diameter×25 cm long), where they cannot move, escape, or turn around, in order to prevent damage to the balloon. Animals are accustomed to this procedure for four days before rectal distension in order to minimize stress reactions during experiments. The balloon used for distension is an arterial embolectomy catheter (Fogarty, Edwards Laboratories Inc.). Rectal distension is performed by insertion of the balloon (2 mm diameter×2 cm long) into the rectum, at 1 cm from the anus, and catheter is fixed at the base of the tail. It is inflated progressively with tepid water by steps of 0.4 ml, from 0 to 1.2 ml, each step of inflation lasting 5 min. To detect possible leakage, the volume of water introduced in the balloon is checked by complete removal with a syringe at the end of the distension period.

The compound of the invention may be administered alone or in combination with one or more other drugs. Generally, it will be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Suitable auxiliary active agents that may be used in combination with the compound of the present invention include:

1) Naturally occurring or synthetic prostaglandins or esters thereof. Suitable prostaglandins for use herein include compounds such as alprostadil, prostaglandin $E_1$, prostaglandin $E_0$, 13, 14-dihydroprosta glandin $E_1$, prostaglandin $E_2$, eprostinol, natural synthetic and semi-synthetic prostaglandins and derivatives thereof including those described in WO-00033825 and/or U.S. Pat. No. 6,037,346 issued on 14 Mar. 2000 all incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3$α, carboprost tromethamine dinoprost, tromethamine, dinoprostone, lipoprost, gemeprost, metenoprost, sulprostone, tiaprost and moxisylate;

2) α-adrenergic receptor antagonist compounds also known as α-adrenoceptors or α-receptors or α-blockers. Suitable compounds for use herein include: the α-adrenergic receptor blockers as described in PCT application WO99/30697 published on 14 Jun. 1998, the disclosures of which relating to α-adrenergic receptors are incorporated herein by reference and include, selective $α_1$-adrenoceptor or $α_2$-adrenoceptor blockers and non-selective adrenoceptor blockers, suitable $α_1$-adrenoceptor blockers include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $α_2$-blocker blockers from U.S. Pat. No. 6,037,346 [14 Mar. 2000] dibenarnine, tolazoline, trimazosin and dibenarnine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptor blockers include: clonidine, papaverine, papaverine hydrochloride, optionally in the presence of a cariotonic agent such as pirxamine;
3) NO-donor (NO-agonist) compounds. Suitable NO-donor compounds for use herein include organic nitrates, such as mono- di or tri-nitrates or organic nitrate esters including glyceryl trinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates,(NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075;
4) Potassium channel openers or modulators. Suitable potassium channel openers/modulators for use herein include nicorandil, cromokalim, levcromakalim, lemakalim, pinacidil, cliazoxide, minoxidil, charybdotoxin, glyburide, 4-amini pyridine, $BaCl_2$;
5) Vasodilator agents. Suitable vasodilator agents for use herein include nimodepine, pinacidil, cyclandelate, isoxsuprine, chloroprumazine, Rec 15/2739, trazodone;
6) Thromboxane A2 agonists;
7) CNS active agents;
8) Ergot alkoloids; Suitable ergot alkaloids are described in U.S. Pat. No. 6,037,346 issued on 14 Mar. 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride;
9) Compounds which modulate the action of natruretic factors in particular atrial naturetic factor (also known as atrial naturetic peptide), B type and C type naturetic factors such as inhibitors or neutral endopeptidase;
10) Compounds which inhibit angiotensin-converting enzyme such as enapril, and combined inhibitors of angiotensin-converting enzyme and neutral endopeptidase such as omapatrilat;
11) Angiotensin receptor antagonists such as losartan;
12) Substrates for NO-synthase, such as L-arginine;
13) Calcium channel blockers such as amlodipine;
14) Antagonists of endothelin receptors and inhibitors or endothelin-converting enzyme;
15) Cholesterol lowering agents such as statins (e.g. atorvastatin/Lipitor-trade mark) and fibrates;
16) Antiplatelet and antithrombotic agents, e.g. tPA, uPA, warfarin, hirudin and other thrombin inhibitors, heparin, thromboplastin activating factor inhibitors;
17) Insulin sensitising agents such as rezulin and hypoglycaemic agents such as glipizide;
18) Acetylcholinesterase inhibitors such as donezipil;
19) Steroidal or non-steroidal anti-inflammatory agents;
20) Estrogen receptor modulators and/or estrogen agonists and/or estrogen antagonists, preferably raloxifene or lasofoxifene, (–)-cis-6-phenyl-5-[4-(2-pyrrolidin-1-yl-ethoxy)-phenyl]-5,6,7,8-tetrahydronaphthalene-2-ol and pharmaceutically acceptable salts thereof the preparation of which is detailed in WO 96/21656;
21) A PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an IC50 against the respective enzyme of less than 100 nM (with the proviso that PDE 3 and 4 inhibitors are only administered topically or by injection to the penis);
22) Vasoactive intestinal protein (VIP), VIP mimetic, VIP analogue, more particularly mediated by one or more of the VIP receptor subtypes VPAC1,VPAC or PACAP (pituitory adenylate cyclase activating peptide), one or more of a VIP receptor agonist or a VIP analogue (e.g. Ro-125-1553) or a VIP fragment, one or more of a α-adrenoceptor antagonist with VIP combination (e.g. Invicorp, Aviptadil);
23) A melanocortin receptor (particularly of the MC3 or MC4 subtype) agonist or modulator or melanocortin enhancer, such as melanotan II, PT-14, PT-141 or compounds claimed in WO-09964002, WO-00074679, WO-09955679, WO-00105401, WO-00058361, WO-00114879, WO-001 13112, WO-09954358;
24) A serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993;
25) A testosterone replacement agent (including dehydroandrostendione), testosternone (Tostrelle), dihydrotestosterone or a testosterone implant;
26) Estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone);
27) A modulator of transporters for noradrenaline, dopamine and/or serotonin, such as bupropion, GW-320659;
28) A purinergic receptor agonist and/or modulator;
29) A neurokinin (NK) receptor antagonist, including those described in WO-09964008;
30) An opioid receptor agonist, antagonist or modulator, preferably agonists for the ORL-1 receptor;
31) An agonist, antagonist or modulator for oxytocin receptors, preferably a selective oxytocin agonist or modulator;
32) Modulators of cannabinoid receptors;
33) A SEP inhibitor (SEPi), for instance a SEPi having an $IC_{50}$ at less than 100 nanomolar, more preferably, at less than 50 nanomolar.

Preferably, the SEP inhibitors according to the present invention have greater than 30-fold, more preferably greater than 50-fold selectivity for SEP over neutral endopeptidase NEP EC 3.4.24.11 and angiotensin converting enzyme (ACE). Preferably the SEPi also has a greater than 100-fold selectivity over endothelin converting enzyme (ECE).

34) An antagonist or modulator for the NPY (particularly Y1 and Y5 subtype) receptor.

35) A Sex Hormone Binding Globulin antagonist or modulator that inhibits estrogens and/or androgens from being bound.

36) An arginase II inhibitor,

37) An agonist, antagonist or modulator for vassopressin receptors, preferably selective for the V1a receptor 38) A PDE5 Inhibitor. Suitable PDE5 inhibitors include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), particularly sildenafil citrate; (6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351 or tadalafil); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one; 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one; 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide (TA-1790); 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide (DA 8159) and pharmaceutically acceptable salts thereof.

39) A selective dopamine D4 receptor agonist such as 2-[(4-pyridin-2-ylpiperazin-1-yl)methyl]-1H-benzimidazole (ABT724).

40) One or more selective seroionin reuptake inhibitors (SSRIs) such as dapoxetine, paroxetine, 3-[(dimethylamino) methyl]-4-[4-(methylsulfanyl)phenoxy]benzenesulfonamide (Example 28, WO 0172687), 3-[(dimethylamino) methyl]-4-[3-methyl-4-(methylsulfanyl)phenoxy] benzenesulfonamide (Example 12, WO 0218333), N-methyl-N-({3-[3-methyl-4-(methylsulfanyl)phenoxy]-4-pyridinyl}methyl)amine (Example 38, PCT Application no PCT/IB02/01032).

41) one or more NEP inhibitors, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat), suitable NEP inhibitor compounds are described in EP-A-1097719; IC50 values against NEP and ACE may be determined using methods described in published patent application EP1097719-A1, paragraphs [0368] to [0376];

42) Melanocortin receptor agonists (e.g. Melanotan II and PT141) and selective MC3 and MC4 agonists (e.g.THIQ).

43) Mono amine transport inhibitors, such as Noradrenaline (norepinephrine) Re-uptake Inhibitors (NRIs), including selective NRIs such as reboxetine, either in its racemic (R,R/S,S) or optically pure (S,S) enantiomeric form, for example (S,S)-reboxetine).

By cross reference herein to compounds contained in patents and patent applications which can be used in accordance with the invention, we mean the therapeutically active compounds as defined in the claims (in particular of claim 1) and the specific examples (all of which is incorporated herein by reference). The above-referenced patents and patent applications are additionally incorporated herein by reference.

If a combination of active agents is administered, then they may be administered simultaneously, separately or sequentially. Pharmaceutical compositions suitable for the delivery of the compound of the present invention and methods for their preparation will be readily apparent to those skilled in the art. Such compositions and methods for their preparation may be found, for example, in *Remington's Pharmaceutical Sciences*, 19th Edition (Mack Publishing Company, 1995), which is incorporated herein by reference.

The compound of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, semisolid or solid matrices or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compound of the invention may also be used in fast-dissolving, fast-disintegrating dosage forms such as those described in Expert Opinion in Therapeutic Patents, 11 (6), 981-986, by Liang and Chen (2001), which is incorporated herein by reference.

For tablet dosage forms, depending on dose, the drug may make up from 0.5 weight % to 80 weight % of the dosage form, more typically from 1 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets, Vol.* 1, by H. Lieberman and L. Lachman (Marcel Dekker, New York, 1980), which is incorporated herein by reference.

Consumable oral films for human or veterinary use are typically pliable water-soluble or water-swellable thin film dosage forms which may be rapidly dissolving or mucoadhesive and typically comprise a compound of the invention, a film-forming polymer, a binder, a solvent, a humectant, a plasticiser, a stabiliser or emulsifier, a viscosity-modifying agent and a solvent. Some components of the formulation may perform more than one function.

The compound of the invention may be water-soluble or insoluble. A water-soluble compound typically comprises from 0.5 weight % to 80 weight %, more typically from 20 weight % to 50 weight %, of the solutes. Less soluble compounds may comprise a greater proportion of the composition, typically up to 88 weight % of the solutes. Alternatively, the compound of the invention may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001), which is incorporated herein by reference. The use of chewing gum to achieve controlled release is described in WO 00/35298, which is incorporated herein by reference.

The compound of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the compound of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus the compound of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(di-lactic-coglycolic)acid (PGLA) microspheres.

The compound of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999), which is incorporated herein by reference.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compound of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as /-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise the compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing the compound of the invention.

The compound of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compound of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

The compound of the invention may be combined with soluble macromolecular entities, such as cyclodextrin and suitable derivatives thereof or polyethylene glycol-containing polymers, in order to improve its solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148, which are incorporated herein by reference.

Inasmuch as it may desirable to administer a combination of active compounds, for example, for the purpose of treating a particular disease or condition, it is within the scope of the present invention that two or more pharmaceutical compositions, at least one of which contains the compound of the invention, may conveniently be combined in the form of a kit suitable for coadministration of the compositions.

Thus the kit of the invention comprises two or more separate pharmaceutical compositions, at least one of which contains the compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Figure 1:
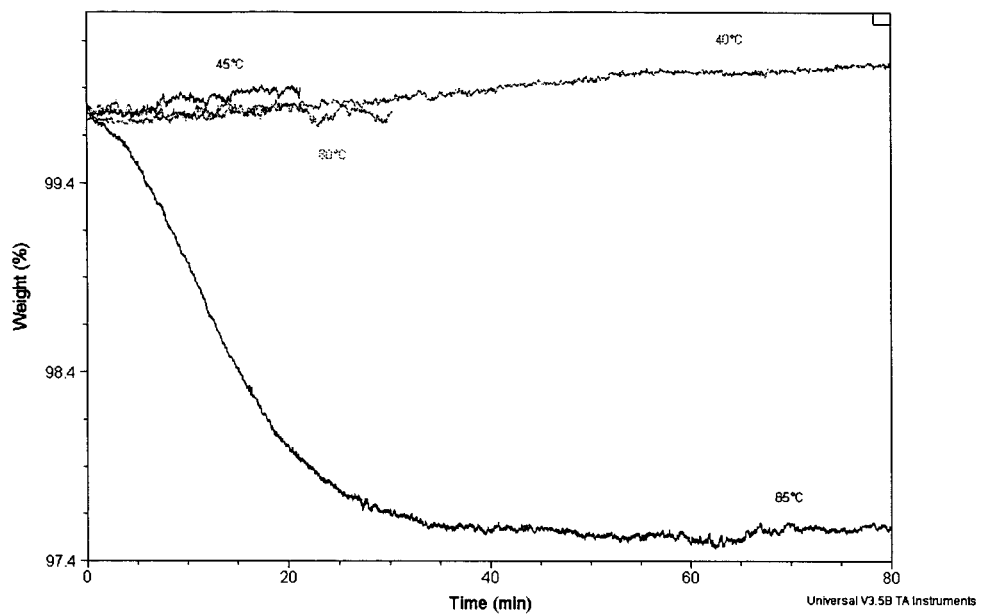
FIG. 1
Figure 2:
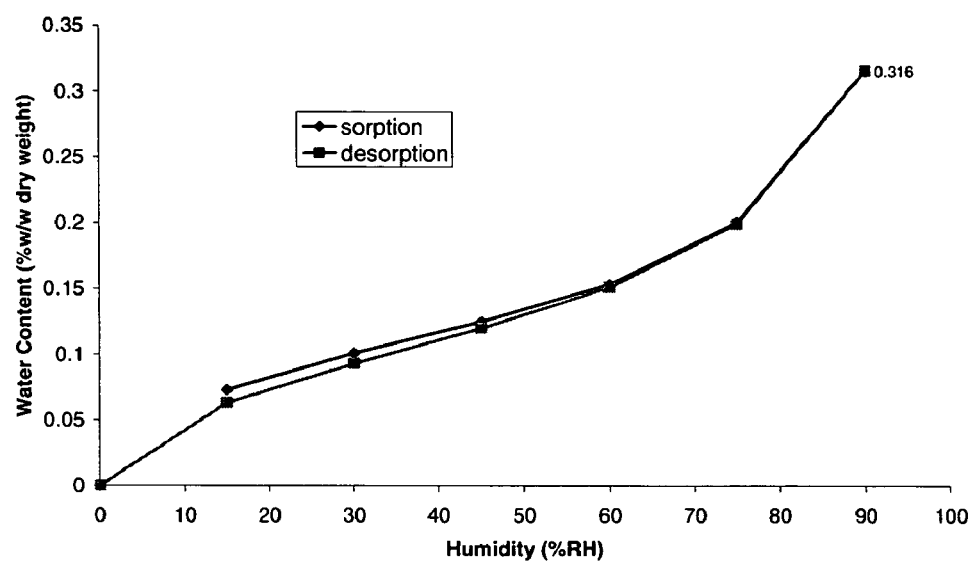
Figure 3:
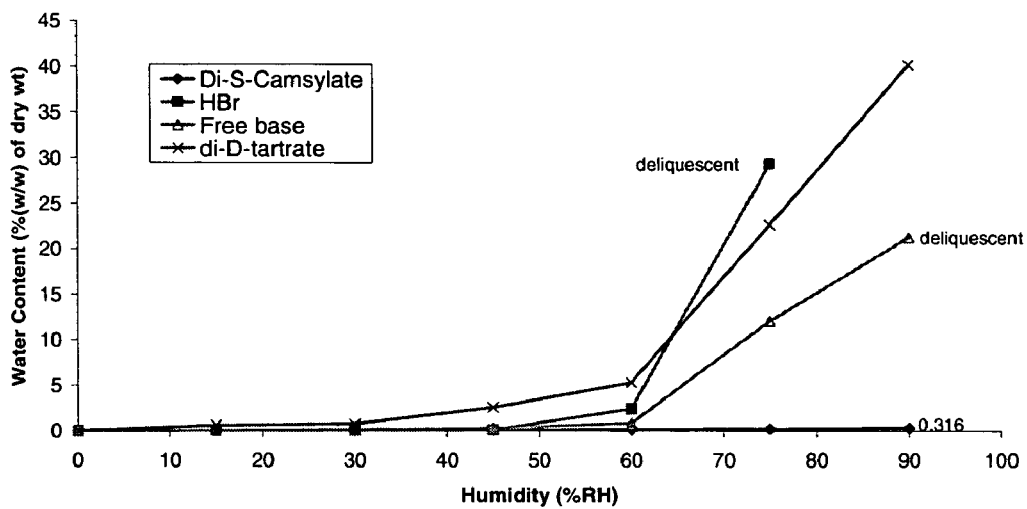
Figure 4:
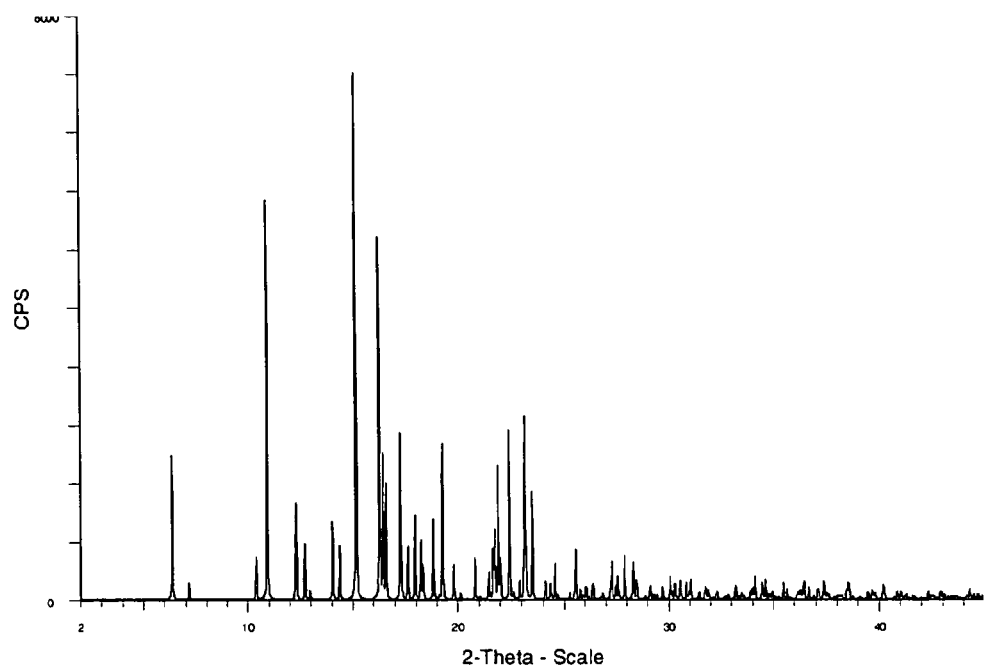
Figure 5:
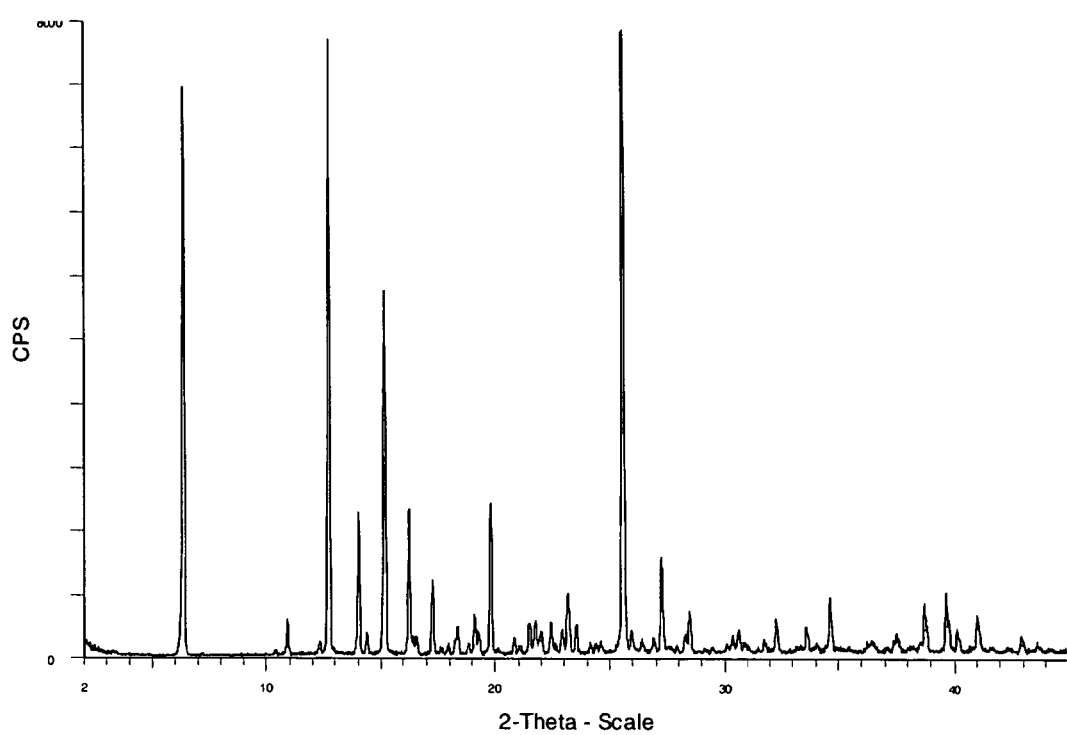
Figure 6:
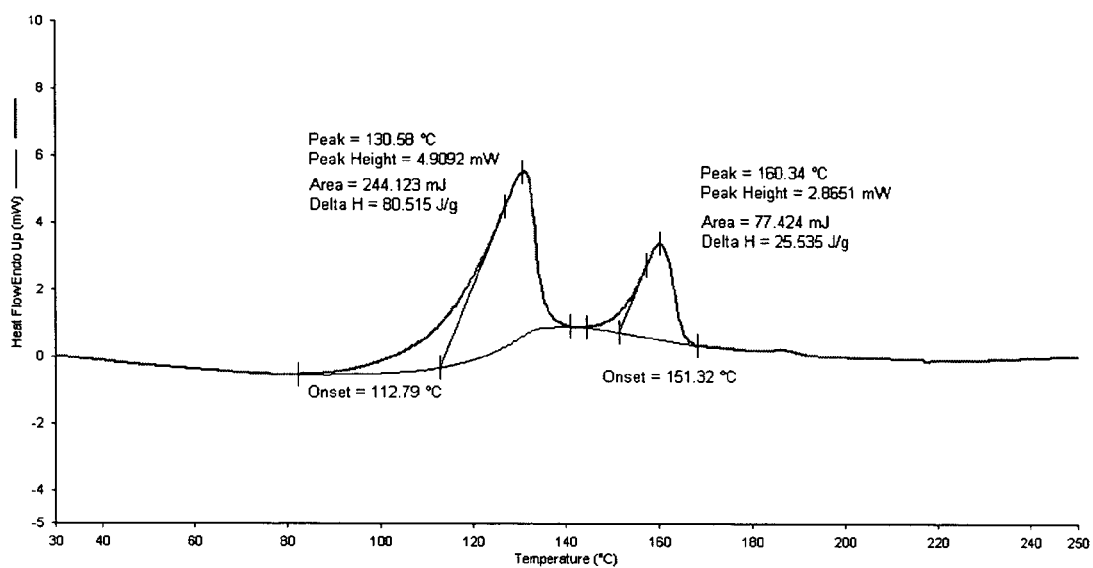

Isothermal gravimetric analysis of 5-[(2R,5S)-5-methyl-4-propylmorpholin-2-yl]pyridin-2-amine di-S-camsylate monohydrate at 40, 45, 80 and 85° C. Material was held at a selected temperature with a 0% RH flow of nitrogen. 5-[(2R,5S)-5-methyl-4-propylmorpholin-2-yl]pyridin-2-amine di S-camsylate salt dehydrates at 85° C., 0% RH. Many hydrates would be lost at 30° C./0% RH.

FIG. 2

Water sorption of 5-[(2R,5S)-5-methyl-4-propylmorpholin-2-yl]pyridin-2-amine di-S-camsylate monohydrate) at 30° C. Sorption at 90% RH is 0.316%(w/w) of dry weight. This value relates to non-bound water and is in addition to that involved in the crystal lattice.

FIG. 3

Comparison of the water sorption of 5-[(2R,5S)-5-methyl-4-propylmorpholin-2-yl]pyridin-2-amine di-S-camsylate monohydrate with the free base, di-D-tartrate, and hydrobromide salt at 30° C.

FIG. 4

Simulated PXRD pattern for 5-[(2R,5S)-5-methyl-4-propylmorpholin-2-yl]pyridin-2-amine di-S-camsylate monohydrate.

FIG. 5

Actual PXRD pattern for 5-[(2R,5S)-5-methyl-4-propylmorpholin-2-yl]pyridin-2-amine di-S-camsylate monohydrate.

FIG. 6

DSC thermogram for 5-[(2R,5S)-5-methyl-4-propylmorpholin-2-yl]pyridin-2-amine di-S-camsylate monohydrate.

EXPERIMENTAL

Differential Scanning Calorimetry (DSC): Differential Scanning Calorimetry was performed using a Perkin Elmer Diamond DSC in aluminium pans with holes and lids. Approximately 3 mg of the samples were heated at 20° C. per minute over a range of 30 to 250° C. with a nitrogen gas purge.

ThermoGravimetric Analysis (TGA): Manufactured by TA instruments, model 2950. Approximately 8 mg of the sample was held at analysis temperature in an open pan with 0% RH nitrogen flow for a minimum of 30 min. Results are representative of the kinetic stability of the hydrate over the period of time the sample was exposed.

Dynamic Vapour Sorption (DVS): Automated Sorption Analyser Model DVS-1. Manufactured by Surface Measurements Systems Ltd. UK. Solid (10-20 mg) is exposed to controlled relative humidity (% RH) environment and the weight change recorded over time. The humidity was stepped from 0 to 90 to 0% RH in 15% RH intervals. A rate of sorption of 0.0005%/min needs to be achieved at each humidity before exposure to the next humidity in the method. When a sample is deliquescent equilibrium sorption is not always achieved.

Powder X-ray Diffraction (PXRD): The PXRD patterns were obtained using a Bruker-AXS Ltd. D5000 powder X-ray diffractometer fitted with an automatic sample changer, a theta-theta goniometer, automatic beam divergence slits, a secondary monochromator and a scintillation counter. The sample was analysed as a powder layer on a silicon wafer specimen mount. The specimen was rotated whilst being irradiated with copper K-alpha$_1$ X-rays (wavelength=1.5406 Ångstroms) with the X-ray tube operated at 40 kV/40 mA. The analyses were performed with the goniometer running in continuous mode set for a 5 second count per 0.02° step over a two theta range of 2° to 55°.

The peaks obtained for 5-[(2R,5S)-5-methyl-4-propylmorpholin-2-yl]pyridin-2-amine di-S-camsylate monohydrate were aligned against those from the calculated pattern from the single crystal structure.

The 2-theta Angles, and relative intensities for the simulated powder pattern were calculated from the single crystal structure using the "Reflex Powder Diffraction" module of Accelrys Materials Studio™ [version 2.2]. Pertinent simulation parameters were in each case:

Wavelength=1.540562 Å (Cu Kα)
Polarisation Factor=0.5
Pseudo-Voigt Profile (U=0.01, V=−0.001, W=0.002)

As will be appreciated by the skilled person, the relative intensities of the various peaks within Tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Tables.

The skilled person will also appreciate that measurements using a different wavelength will result in different shifts according to the Bragg equation $-n\lambda=2d \sin \theta$.

Such further PXRD patterns generated by use of alternative wavelengths are considered to be alternative representations of the PXRD patterns of the crystalline materials of the present invention and as such are within the scope of the present invention.

The compound of the invention may be synthesised according to the procedures below. Where preparations have been carried out on differing scales, suitable methods for performing both the large and smaller scale syntheses are given. The following abbreviations and definitions are used:

| | |
|---|---|
| TBME | tertiary-Butyl methyl ether |
| DCM | Dichloromethane |
| IPA | Isopropyl alcohol |
| m/z | mass spectrum peak |
| HCl | Hydrochloric acid |
| NaOH | Sodium hydroxide |
| MS | mass spectrum |
| m | Multiplet |
| q | Quartet |
| s | Singlet |
| t | Triplet |
| br | Broad |
| Kg | Kilograms |
| L | Liter |
| g | grams |
| CDCl$_3$ | deuterated chloroform |
| ppm | Parts per million |

NMR spectra were obtained using a Varian Inova 300 MHz spectrometer by dissolving the sample in an appropriate solvent.

Mass spectra were obtained using an LC-MS system consisting of a Thermo-Finnigan Surveyor HPLC system in combination with a Thermo Finnigan LCQ ion-trap mass spectrometer 5-Bromo-2-(2,5-dimethylpyrrol-1-yl)pyridine

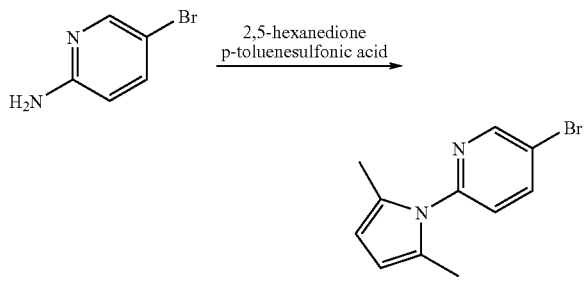

2-Amino-5-bromopyridine (6.0 Kg, 34.7 mol), 2,5-hexanedione (4.35 Kg, 38.2 mol) and p-toluenesulfonic acid (12 g) were dissolved in heptane (36 L) and refluxed under Dean Stark conditions overnight. The equipment was set for distillation and heptane (18 L) was removed by distillation. The mixture was cooled to 20° C. for 60 minutes. Seed crystals were added and the mixture granulated at 20° C. for 2 hours and then at 5° C. overnight. The product was collected by filtration, washed with heptane (2×6 L) and dried at 45° C. under vacuum overnight. Yield=80% (7.0 Kg) δ$_H$ (CDCl$_3$ 300 MHz) 2.20 (6H, s), 5.95 (2H, s), 7.15 (1H, d), 7.95 (1H, d), 8.70 (1H, s) ppm. MS m/z 253 (MH$^+$, Br isotope).

2-Chloro-1-[6-(2,5-dimethylpyrrol-1-yl)pyridin-3-yl]ethanone

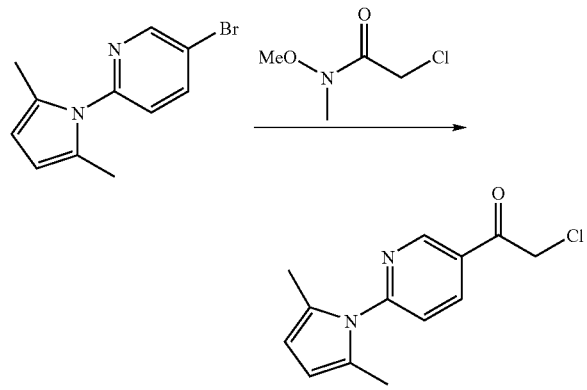

A solution of 5-bromo-2-(2,5-dimethylpyrrol-1-yl)pyridine (1.00 Kg 3.98 mol) in TBME (7.5 L) was cooled to −70° C. n-Butyl lithium (2.5N in hexane; 1.73 L, 4.32 mol) was added drop-wise over 1 hour maintaining the temperature between −74° C. and −69° C. The mixture was then stirred at a temperature between −74° C. and −69° C. for a further 15 minutes. A solution of 2-chloro-N-methoxy-N-methylacetamide (0.65 Kg, 4.72 mol) in TBME (3.0 L) was then added drop-wise over 100 minutes maintaining the temperature between −73° C. and −67° C. The resulting mixture was then stirred at temperature between −73 and −67° C. for a further 100 minutes. 2N HCl (5.0 L) was then added drop-wise over 45 minutes, allowing the temperature to rise from −70° C. to 17° C. during the addition. TBME (4.0 L) and water (2.0 L) was added to the resulting suspension and the mixture was stirred before allowing the phases to separate. The organic layer was washed with water (2.0 L), and aqueous NaHCO$_3$ (0.13 Kg in 2.0 L of water) and water (2.0 L) before concentrating in vacuo. IPA (1.50 L) was added to the residue and the mixture was heated to reflux. The mixture was then allowed to cool to room temperature and stirred overnight, before cooling to 8-12° C. for 1 hour. The product was collected by filtration, washed with IPA (2×0.1 L) and dried at 45° C. under vacuum overnight. Yield 78.8% (0.78 Kg), δ$_H$ (CDCl$_3$, 300 MHz) 2.20 (6H, s), 4.70 (2H, s), 5.95 (2H, s), 7.35 (1H, d), 8.40 (1H, dd), 9.15 (1H, d) ppm. MS m/z 249 (MH$^+$).

2-(2,5-Dimethylpyrrol-1-yl)-5-oxiranylpyridine

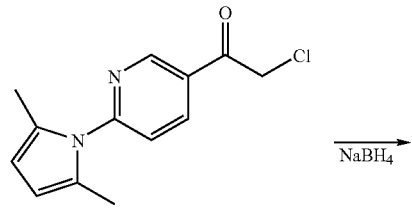

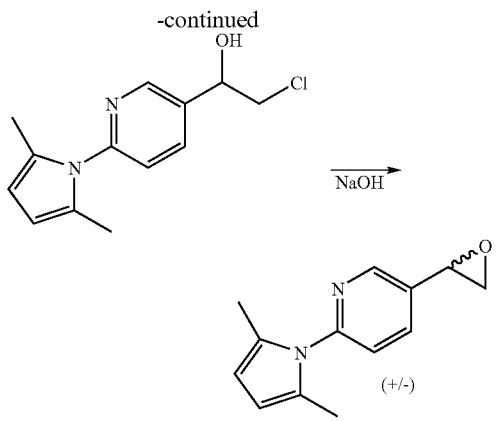

Water (1.08 Kg) was added dropwise to a suspension of sodium borohydride (0.17 Kg, 4.36 mol) in 1,4-dioxane (6.49 L) at 16° C. and the resulting solution stirred at room temperature. A solution of 2-chloro-1-[6-(2,5-dimethylpyrrol-1-yl)pyridin-3-yl]ethanone (1.08 Kg, 4.35 mol) in tetrahydrofuran (2.16 L) was added over 1 hour and the resulting solution stirred for 45 minutes at room temperature. When all the 2-chloro-1-[6-(2,5-dimethylpyrrol-1-yl)pyridin-3-yl]ethanone was consumed the reaction mixture was cooled to 19° C. and treated with concentrated HCl (36% w/w) (1.08 L) over 40 minutes. The mixture was cooled to 11° C. and NaOH (32% w/w) (1.64 L) was added over 45 minutes maintaining the temperature below 25° C. The mixture was then allowed to granulate at room temperature overnight. When all the chloroalcohol intermediate was consumed, DCM (5.0 L) and water (5.0 L) were added and the mixture was stirred before allowing the phases to separate. The aqueous phase was extracted with DCM (2.50 L) and the combined organic phases were washed with water (2×1.0 L) and concentrated in vacuo. Yield 98% (0.92 Kg) δ$_H$ (CDCl$_3$, 300 MHz) 2.10 (6H, s), 2.90 (1H, dd), 3.25 (1H, dd), 4.00 (1H, dd), 5.90 (2H, s), 7.20 (1H, d), 7.70 (1H, dd), 8.40 (1H, d) ppm. MS m/z 215 (MH$^+$).

(2S)-2-[{(RS)-2-[6-(2,5-dimethyl-1H-pyrrol-1-yl)pyridin-3-yl]-2-hydroxyethyl}propylamino]propan-1-ol

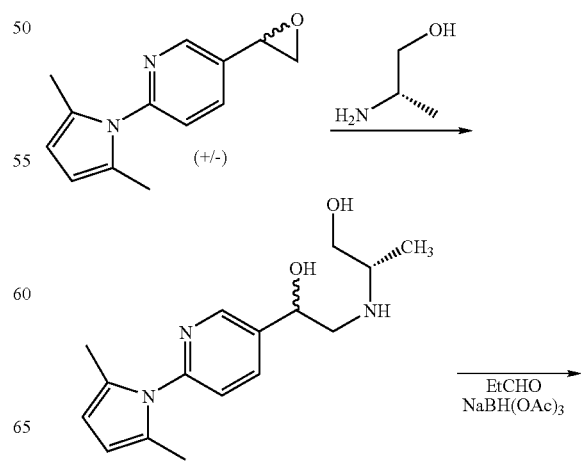

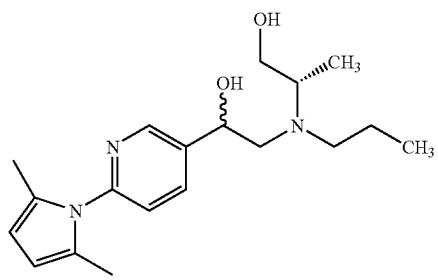

A mixture of 2-(2,5-dimethylpyrrol-1-yl)-5-oxiranylpyridine (0.65 Kg, 3.04 mol), (S)-(+)-2-amino-1-propanol (0.30 Kg, 3.95 mol) in toluene (6.50 L) was heated to reflux overnight. The reaction mixture was cooled to room temperature and DCM (6.5 L) and water (1.30 L) were added and the phases allowed to separate. Sodium triacetoxyborohydride (0.96 Kg, 4.56 mol) was added to the organic layer, followed by propionaldehyde (0.48 L, 6.68 mol) and glacial acetic acid (0.17 L, 3.04 mol) dropwise maintaining the temperature below 30° C. The reaction mixture was stirred at room temperature for 1 hour before quenching with water (1.20 L) and an aqueous solution of potassium carbonate (1.00 Kg in 3.23 Kg water) and the phases were allowed to separate. The aqueous phase was extracted with DCM (1.20 L) and the combined organic phases washed with water (0.60 L), water (0.30 L) and concentrated in vacuo. Yield 89% (0.89 Kg, the material was isolated in approximately 70% purity) $\delta_H$ (CDCl$_3$, 300 MHz) 0.8-1.0 (6H, m), 1.50-1.70 (2H, m), 2.10 (6H, s), 2.50-3.15 (5H, m), 3.50 (2H, dd), 4.80 (1H, dd), 5.90 (2H, s), 7.20 (1H, m), 7.80-7.90 (1H, m), 8.60 (1H, m) ppm. MS m/z 332 (MH$^+$). The intermediate amine was characterised as $\delta_H$ (CDCl$_3$, 300 MHz) 1.10 (3H, t), 2.10 (6H, s), 2.7-3.2 (3H, m), 3.45 (1H, m), 3.70 (H, dd), 4.85 (1H, m), 5.90 (2H, s), 7.20 (1H, d), 7.90 (1H, dd), 8.60 (1H, d) ppm. MS m/z 290 (MH$^+$).

(2S)-2-[{(RS)-2-[6-(2,5-dimethyl-1H-pyrrol-1-yl)pyridin-3-yl]-2-hydroxyethyl}amino]propan-1-ol

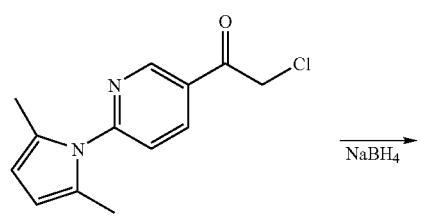

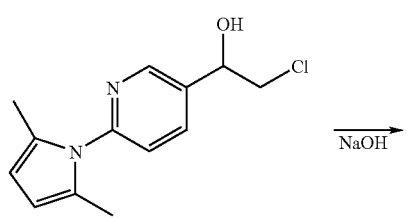

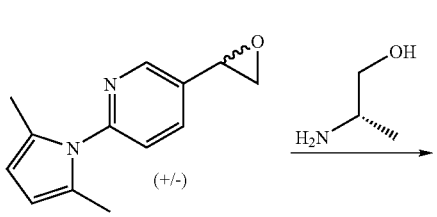

Water (15.0 L) was added to a suspension of sodium borohydride (4.11 Kg, 109 mol) in tetrahydrofuran (140 L) at 15° C. and the resulting solution stirred at 15° C. A solution of 2-chloro-1-[6-(2,5-dimethylpyrrol-1-yl)pyridin-3-yl]ethanone (30.0 Kg, 120.6 mol) in tetrahydrofuran (100 L) and water (15 L) was added over 40 minutes maintaining the temperature below 30° C. The resulting solution was stirred for 60 minutes at 15° C. When all the 2-chloro-1-[6-(2,5-dimethylpyrrol-1-yl)pyridin-3-yl]ethanone was consumed the reaction mixture was treated with concentrated HCl (27% w/w, 47 Kg) over 80 minutes maintaining the temperature below 30° C. The mixture was cooled to 15° C. and NaOH (34% w/w, 79 Kg) was added over 60 minutes maintaining the temperature below 30° C. The mixture was then granulated at 20° C. overnight. When all the chloroalcohol intermediate was consumed, the aqueous phase was separated. DCM (150 L) and water (140 L) were added and the mixture was stirred before allowing the phases to separate. The organic phase was washed with water (2×30 L). (S)-(+)-2-amino-1-propanol (17.2 Kg, 229 mol) and tetrahydrofuran (15 L) were added over 20 minutes. The equipment was set for distillation and DCM was replaced by tetrahydrofuran to give a final volume of 160 litres. The reaction mixture was left at reflux overnight. After cooling to room temperature, DCM (150 L) was added and the mixture was washed with water (3×30 L). The equipment was set for distillation and the tetrahydrofuran and DCM were replaced by acetonitrile to give a final volume of 84 litres. ααα-trifluorotoluene (300 L) was added over 60 minutes, the mixture was cooled to 5° C. over 8 hours and granulated at 5° C. for 6 hours. The product was collected by filtration, washed with ααα-trifluorotoluene (2×30 L) and dried at 45° C. under vacuum overnight. Yield=65% (22.7 Kg) $\delta_H$ (CDCl$_3$, 300 MHz) 1.10 (3H, t), 2.10 (6H, s), 2.7-3.2 (3H, m), 3.45 (1H, m), 3.70 (H, dd), 4.85 (1H, m), 5.90 (2H, s), 7.20 (1H, d), 7.90 (1H, dd), 8.60 (1H, d) ppm. MS m/z 290 (MH$^+$). The intermediate epoxide was characterised as $\delta_H$ (CDCl$_3$, 300 MHz) 2.10 (6H, s), 2.90 (1H, dd), 3.25 (1H, dd), 4.00 (1H, dd), 5.90 (2H, s), 7.20 (1H, d), 7.70 (1H, dd), 8.40 (1H, d) ppm. MS m/z 215 (MH$^+$).

(2S)-2-[{(RS)-2-[6-(2,5-dimethyl-1H-pyrrol-1-yl)pyridin-3-yl]-2-hydroxyethyl}propylamino]propan-1-ol

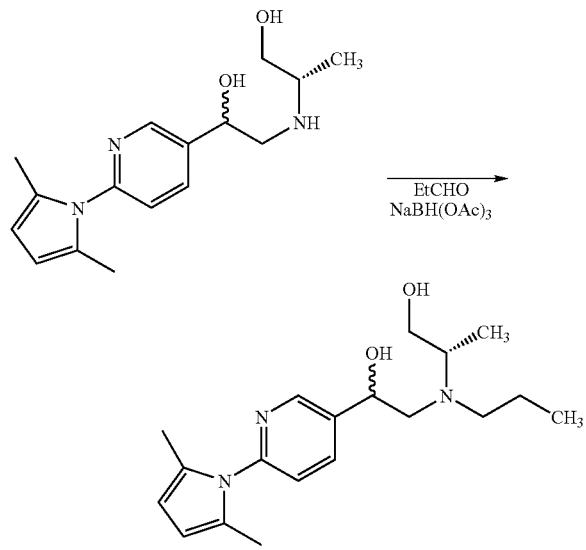

Propioanaldehyde (5.02 Kg, 86.4 mol) was added over 10 minutes to a solution of (2S)-2-[{(RS)-2-[6-(2,5-dimethyl-1H-pyrrol-1-yl)pyridin-3-yl]-2-hydroxyethyl} amino]propan-1-ol (22.7 Kg, 78.6 mol) in DCM (123 L) at 20° C. The resulting solution was stirred at 20° C. for 2 hours and then allowed to settle before adding it to a suspension of sodium triacetoxyborohydride (25.8 Kg, 122 mol) in DCM (123 L) over 90 minutes maintaining the temperature below 30° C. The reaction mixture was stirred at 20° C. for 1 hour before quenching with an aqueous solution of potassium carbonate (36.4 Kg in 136 L of water) and the phases were allowed to separate. The organic phase was washed with water (2×23 L). The equipment was set for distillation and DCM (190 L) was removed by distillation to give a final volume of 45 litres. The mixture was cooled to 20° C. Yield 100% (51.1 Kg, 50.9% w/w in DCM). $\delta_H$ (CDCl$_3$, 300 MHz) 0.8-1.0 (6H, m), 1.50-1.70 (2H, m), 2.10 (6H, s), 2.50-3.15 (5H, m), 3.50 (2H, dd), 4.80 (1H, dd), 5.90 (2H, s), 7.20 (1H, m), 7.80-7.90 (1H, m), 8.60 (1H, m) ppm. MS m/z 332 (MH$^+$).

(2S)-2-[{(RS)-2-[6-aminopyridin-3-yl)-2-hydroxyethyl}(propyl)amino]propan-1-ol

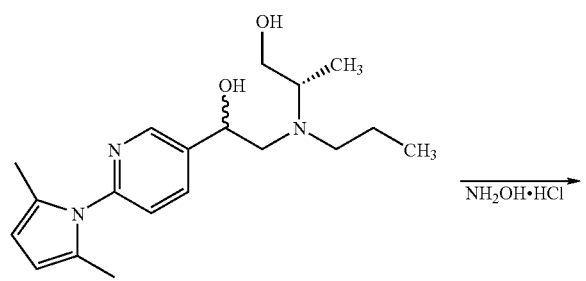

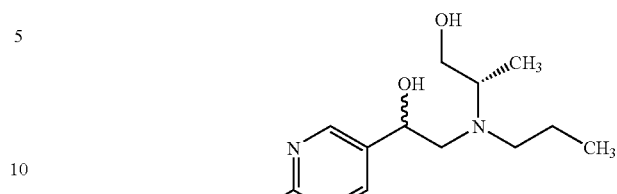

(2S)-2-[{(R,S)-2-[6-(2,5-dimethyl-1H-pyrrol-1-yl)pyridin-3-yl]-2-hydroxyethyl}propylamino]propan-1-ol (0.90 Kg, 2.71 mol), hydroxylamine hydrochloride (0.56 Kg, 8.05 mol), ethanol (5.20 L) and water (0.45 L) were combined and heated to reflux overnight. The reaction mixture was cooled to room temperature and concentrated in vacuo. Water (1.50 L) was added and the suspension cooled to 5° C. The resulting suspension was added portionwise to a mixture of concentrated HCl (36% w/w, 0.25 L) and water (3.10 L). DCM (1.00 L) was added and the phases were allowed to separate. The aqueous phase was washed with DCM (2×0.40 L) before combining with DCM (1.60 L) and basifying with NaOH 10N (1.45 L). After separating the phases the aqueous phase was extracted with DCM (1.60 L) and the combined organic phase washed with NaOH 1.4N (0.70 L), NaOH 0.9N (0.55 L), water (0.50 L), water (0.25 L) and concentrated in vacuo. Yield 87% (0.55 Kg).

(2S)-2-[{(R,S)-2-[6-(2,5-dimethyl-1H-pyrrol-1-yl)pyridin-3-yl]-2-hydroxyethyl}propylamino]propan-1-ol (51.1 Kg, 50.9% w/w in DCM, 78.5 mol), hydroxylamine hydrochloride (16.4 Kg, 236 mol), sodium bicarbonate (3.30 Kg, 39.3 mol) and ethanol (136 L) were combined. The equipment was set for distillation and DCM was replaced by ethanol to give a final volume of 130 litres. The reaction mixture was cooled to room temperature and held overnight at this temperature. The reaction mixture was heated to reflux and stirred for 10.5 hours at reflux before cooling to room temperature. The equipment was set for vacuum distillation and ethanol was replaced by water to give a final volume of 120 litres. The mixture was cooled to room temperature and granulated overnight. The by-product was isolated by filtration and washed with water (13 L). The filtrate was acidified with HCl (22% w/w, 13.2 Kg) and washed with DCM (3×26 L) before combining with DCM (78 L), water (39 L) and basifying with NaOH (40% w/w, 38.7 Kg). After separating the phases the aqueous phase was extracted with DCM (52 L) and the combined organic phase washed with NaOH (4.4% w/w, 14.6 Kg) and water (2×9 L). Yield 93% (196.3 Kg, 9.5% w/w in DCM).

$\delta_H$ (CDCl$_3$, 300 MHz), 0.85 (3H, t), 0.95 (3H, m) 1.40-1.60 (2H, m), 2.40-2.80 (4H, m), 2.95-3.10 (1H, m), 3.40 (1H, d), 3.45 (1H, d), 4.45 (2H, br), 4.55 (1H, m), 6.50 (1H, d), 7.45 (1H, d), 8.00 (1H, s) ppm. MS m/z 254 (MH$^+$).

5-[(2R,5S)-5-methyl-4-propylmorpholin-2-yl]pyridin-2-amine (Compound A) and 5-[(2S,5S)-5-methyl-4-propylmorpholin-2-yl]pyridin-2-amine (Compound B)

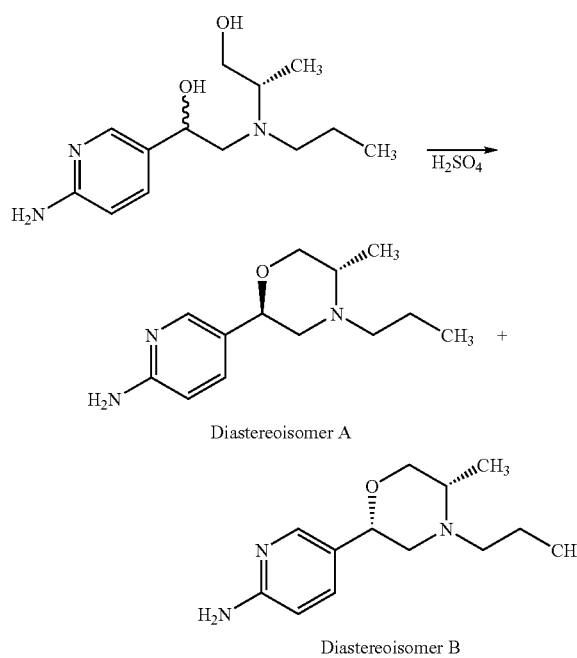

Diastereoisomer A

Diastereoisomer B

A solution of (2S)-2-[{(2RS)-2-[6-aminopyridin-3-yl)-2-hydroxyethyl}(propyl)amino]propan-1-ol (0.50 Kg, 1.97 mol) in DCM (1.0 L) was added portionwise to concentrated sulphuric acid (98% w/w) (1.10 L) maintaining the temperature below 25° C. The mixture was stirred at room temperature for 1 hour and then cooled to between 5° C. and 10° C. Water (2.0 L) was added dropwise and the phases allowed to separate. The aqueous phase was washed with DCM (0.5 L) and then added dropwise to a solution of NaOH (1.71 Kg) in water (11.0 L). DCM (1.5 L) was added and the phases allowed to separate. The aqueous phase was extracted with DCM (0.5 L) and the combined organic phase washed with water (0.5 L), water (2×0.25 L) and concentrated in vacuo. Yield 82% (0.38 Kg).

(2S)-2-[{(2RS)-2-[6-aminopyridin-3-yl)-2-hydroxyethyl}(propyl)amino]propan-1-ol in DCM (9.04% w/w, 340.6 Kg, 122 mol) was added over 3.5 hours to concentrated sulphuric acid (98% w/w, 119.4 Kg, 1217 mol) maintaining the temperature below 30° C. The mixture was stirred at room temperature for 1 hour and then cooled to 5° C. Water (145 L) was added over 2 hours maintaining the temperature below 30° C. and the phases allowed to separate. To the aqueous phase was added DCM (92 L) and aqueous ammonia (35% w/w, 130 Kg, 2678 mol) over 2 hours maintaining the temperature below 30° C. After separating the phases, the aqueous phase was extracted with DCM (31 L) and the combined organic phase washed with water (2×16 L). The equipment was set for distillation and DCM was replaced by acetone to give a final volume of 120 litres. Yield 92.5% (123.3 Kg, 21.5% w/w in acetone).

$\delta_H$ (CDCl$_3$, 300 MHz), 0.85 (3H, 2t), 1.00 (3H×0.45, d, diastereoisomer A), 1.10 (3H×0.55, d, diastereoisomer B) 1.40-1.60 (2H, m), 2.20-2.90 (5H, m), 3.30-3.90 (2H, m), 4.20 (2H, br), 4.20-4.30 (1H, m), 6.50 (1H, m), 7.45 (1H, m), 8.05 (1H, m) ppm. MS m/z 236 (MH$^+$).

The ratio of diastereoisomer A and diastereoisomer B is determined by 1H-NMR after measuring the ratio of $\delta_H$ 1.00 ppm and $\delta_H$ 1.10 ppm signals.

5-[(2R,5S)-5-methyl-4-propylmorpholin-2-yl]pyridine-2-amine, di((1S)-10-camphorsulfonate)monohydrate

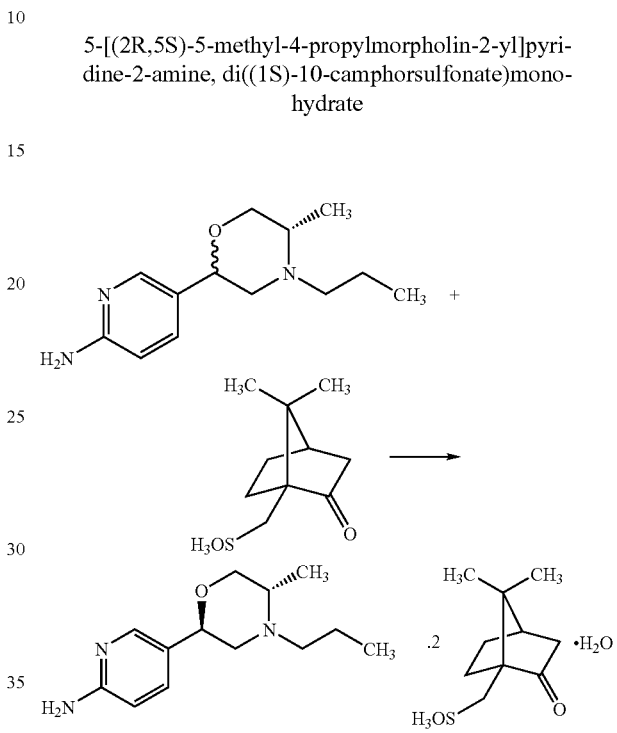

To a solution of 5-[(2S,5S)-5-methyl-4-propylmorpholin-2-yl]pyridine-2-amine and 5-[(2R,5S)-5-methyl-4-propylmorpholin-2-yl]pyridine-2-amine (2.62 Kg, 11.1 mol) in acetone (31.4 L) was added a solution of (1S)-10-camphorsulfonic acid (5.11 Kg, 22.0 mol) in water (2.29 L) and acetone (5.24 L). The solution was stirred at 20° C. for 15 minutes, seed crystals were added and the mixture was granulated at 20° C. overnight. The product was collected by filtration, washed with acetone (2×2.6 L) and dried at 40° C. under vacuum overnight. Yield 34% (2.71 Kg).

To a solution of 5-[(2S,5S)-5-methyl-4-propylmorpholin-2-yl]pyridine-2-amine and 5-[(2R,5S)-5-methyl-4-propylmorpholin-2-yl]pyridine-2-amine (143.7 Kg, 21.5% w/w in acetone, 131 mol) in acetone (343 L) was added a solution of (1S)-10-camphorsulfonic acid (63.3 Kg, 256 mol) in water (24 L). The solution was stirred at 20° C. for 15 minutes, seed crystals were added and the mixture was granulated at 20° C. overnight. The product was collected by filtration, washed with acetone (62 L) and dried at 45° C. under vacuum overnight. Yield 37.8% (35.6 Kg).

$\delta_H$ (CDCl$_3$, 300 MHz) 0.7 (6H, s), 0.9 (3H, t), 1.05 (6H, s), 1.2-1.35 (7H, m), 1.5-1.75 (2H, m), 1.8 (2H, d), 1.8-1.9 (2H, m), 1.95 (2H, m), 2.25 (2H, m), 2.40 (2H, d), 2.55-2.7 (2H, m), 2.90 (2H, d), 2.95-3.35 (5H, m), 3.65 (1H, m), 4.10 (1H, m), 4.7 (1H, m), 7.0 (1H, d), 7.95 (2H, m), 8.15 (2H, br), 9.8 (2H, br) ppm. MS m/z 236 (MH$^+$).

Characteristic PXRD Peaks from Calculated Pattern for 5-[(2R,5S)-5-methyl-4-propylmorpholin-2-yl]pyridin-2-amine di-S-camsylate monohydrate Main characteristic peaks:

| Angle 2-Theta (Degrees) | Intensity (%) |
| --- | --- |
| 6.3 | 27.3 |
| 10.9 | 75.9 |
| 12.3 | 18.3 |
| 12.7 | 10.7 |
| 14.0 | 15.0 |
| 14.4 | 10.2 |
| 15.1 | 100.0 |
| 16.3 | 68.8 |
| 16.4 | 28.0 |
| 16.6 | 22.1 |
| 17.3 | 31.6 |
| 17.6 | 9.9 |
| 18.0 | 15.9 |
| 18.8 | 15.4 |
| 19.3 | 29.6 |
| 21.7 | 13.5 |
| 21.9 | 25.9 |
| 22.4 | 32.2 |
| 23.2 | 35.0 |
| 23.5 | 20.4 |
| 25.6 | 9.4 |
| 27.9 | 8.5 |

Characteristic PXRD Peaks for 5-[(2R,5S)-5-methyl-4-propylmorpholin-2-yl]pyridin-2-amine di-S-camsylate monohydrate

| Angle 2-Theta (Degrees) | Intensity (%) |
| --- | --- |
| 6.3 | 90.6 |
| 10.9 | 6.1 |
| 12.7 | 98.3 |
| 14.0 | 23.1 |
| 15.1 | 58.4 |
| 16.3 | 23.6 |
| 17.3 | 12.4 |
| 19.1 | 7.1 |
| 19.8 | 24.5 |
| 21.7 | 5.8 |
| 23.2 | 10.2 |
| 25.6 | 100.0 |
| 27.2 | 15.8 |
| 28.5 | 7.6 |
| 32.3 | 6.1 |
| 34.7 | 9.7 |
| 38.7 | 8.8 |
| 39.7 | 10.5 |
| 39.8 | 6.0 |
| 41.1 | 7.1 |
| 46.9 | 10.5 |
| 47.0 | 6.0 |

The invention claimed is:

1. 5-[(2R,5S)-5-methyl-4-propylmorpholin-2-yl]pyridin-2-amine di-S-camsylate:

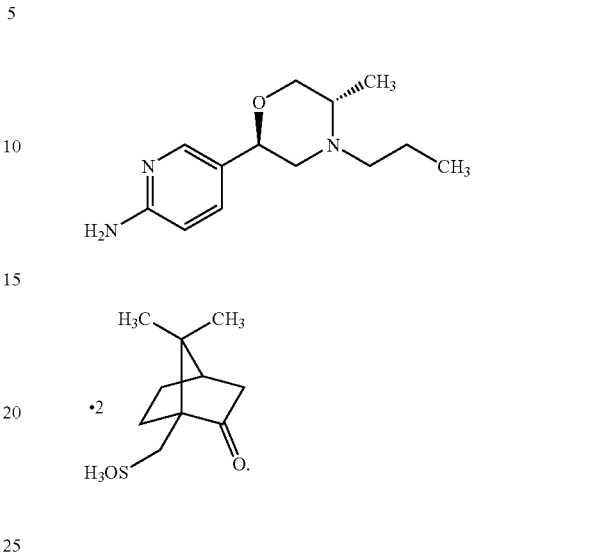

2. The compound according to claim 1 in the form of a monohydrate.

3. The compound according to claim 2 having characteristic main peaks in its powder X-ray diffraction pattern, generated using copper K-alpha$_1$ X-ray (wavelength=1.54056 Angstroms), of 6.3, 12.7, 15.1, 16.3 and 25.6 degrees 2θ.

4. A pharmaceutical composition comprising 5-[(2R,5S)-5-methyl-4-propylmorpholin-2-yl]pyridin-2-amine di-S-camsylate and a pharmaceutically acceptable diluent or carrier.

5. The pharmaceutical composition according to claim 4, wherein 5-[(2R,5S)-5-methyl-4-propylmorpholin-2-yl]pyridin-2-amine di-S-camsylate is in the form of a monohydrate.

6. A compound of formula (VII)

(VII)

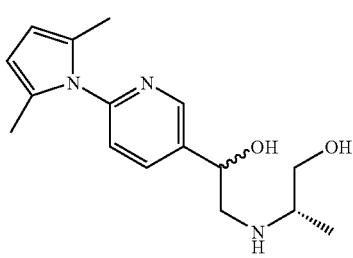

and pharmaceutically acceptable salts and solvates thereof.

* * * * *